United States Patent
Daloz et al.

(10) Patent No.: US 11,806,752 B2
(45) Date of Patent: Nov. 7, 2023

(54) ULTRASOUND TRANSDUCER AND METHOD FOR WAFER LEVEL FRONT FACE ATTACHMENT

(71) Applicant: General Electric Company, Schenectady, NY (US)

(72) Inventors: Flavien Daloz, Antibes (FR); Philippe Menage, Vence (FR); Edouard Da Cruz, Nice (FR); Jean Pierre Malacrida, Saint Laurent (FR); Giandonato Stallone, Nice (FR); Coraly Cuminatto, Le Cannet (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 786 days.

(21) Appl. No.: 16/783,900

(22) Filed: Feb. 6, 2020

(65) Prior Publication Data

US 2020/0171543 A1 Jun. 4, 2020

Related U.S. Application Data

(62) Division of application No. 15/385,620, filed on Dec. 20, 2016, now Pat. No. 10,596,598.

(51) Int. Cl.
*H10N 30/50* (2023.01)
*H10N 30/088* (2023.01)
*B06B 1/06* (2006.01)
*A61B 8/12* (2006.01)
*A61B 8/00* (2006.01)

(52) U.S. Cl.
CPC .......... *B06B 1/0644* (2013.01); *B06B 1/0622* (2013.01); *H10N 30/088* (2023.02); *H10N 30/50* (2023.02); *A61B 8/12* (2013.01); *A61B 8/4483* (2013.01)

(58) Field of Classification Search
CPC ... B06B 1/0622; B06B 1/0644; A61B 8/4483; A61B 8/12; H01L 41/083; H01L 41/09; H01L 41/29; H01L 41/338
See application file for complete search history.

(56) References Cited

U.S. PATENT DOCUMENTS

| 4,385,255 A * | 5/1983 | Yamaguchi | .......... B06B 1/0622 29/25.35 |
| 4,747,192 A * | 5/1988 | Rokurota | .............. B06B 1/0629 29/25.35 |

(Continued)

FOREIGN PATENT DOCUMENTS

| EP | 2366460 A2 * | 9/2011 | .......... G01N 29/043 |
| WO | WO-9421388 A1 * | 9/1994 | .......... A61B 8/4483 |

*Primary Examiner* — Jeffrey T Carley
(74) *Attorney, Agent, or Firm* — McCoy Russell LLP

(57) ABSTRACT

Methods and systems are provided for a single element ultrasound transducer. In one embodiment, a method for the transducer comprises laminating a comb structure and a conductive base package into an acoustic stack with a non-conductive glue, grinding the acoustic stack, and dicing the ground acoustic stack along a plane extending from the top surface of the second fin of the conductive base package to the bottom surface of the acoustic stack. The resulting transducer may have a flat front face with a non-conductive groove separating a ground pad formed by the conductive base package from a signal pad formed by a matching layer of the comb structure.

13 Claims, 10 Drawing Sheets

(56) References Cited

U.S. PATENT DOCUMENTS

| | | | | |
|---|---|---|---|---|
| 5,027,822 | A * | 7/1991 | Gelly | B06B 1/0622 29/25.35 |
| 5,239,736 | A * | 8/1993 | Sliwa, Jr. | B06B 1/06 29/418 |
| 5,704,105 | A * | 1/1998 | Venkataramani | B06B 1/064 29/25.35 |
| 6,537,224 | B2 * | 3/2003 | Mauchamp | A61B 8/00 29/25.35 |
| 7,148,607 | B2 * | 12/2006 | Sato | B06B 1/064 310/366 |
| 7,764,006 | B2 * | 7/2010 | Tsukamura | B41J 2/1631 310/334 |
| 7,905,007 | B2 * | 3/2011 | Calisti | B06B 1/0618 29/609.1 |
| 7,908,721 | B2 * | 3/2011 | Zipparo | B06B 1/0629 29/25.35 |
| 10,561,398 | B2 | 2/2020 | Daloz et al. | |
| 2005/0099096 | A1 * | 5/2005 | Baumgartner | H01L 41/277 310/334 |
| 2007/0222339 | A1 | 9/2007 | Lukacs et al. | |
| 2008/0238259 | A1 * | 10/2008 | Osawa | H01L 41/293 310/334 |
| 2009/0069689 | A1 * | 3/2009 | Isono | B06B 1/0629 600/459 |
| 2009/0108708 | A1 * | 4/2009 | Jiang | B06B 1/0622 29/25.35 |
| 2010/0066207 | A1 * | 3/2010 | Saito | A61B 8/4281 310/335 |
| 2012/0007472 | A1 | 1/2012 | Tai et al. | |
| 2012/0118475 | A1 * | 5/2012 | Baumgartner | H03H 3/08 156/247 |
| 2012/0157853 | A1 * | 6/2012 | Gelly | A61B 8/4427 600/459 |
| 2013/0327155 | A1 | 12/2013 | Drachmann | |
| 2014/0132114 | A1 * | 5/2014 | Fukase | B06B 1/06 310/322 |
| 2014/0187965 | A1 | 7/2014 | Reiter | |
| 2014/0375171 | A1 * | 12/2014 | Tai | B06B 1/0622 29/25.35 |
| 2015/0345987 | A1 | 12/2015 | Hajati | |
| 2017/0288638 | A1 * | 10/2017 | Wildes | H01L 41/277 |

* cited by examiner

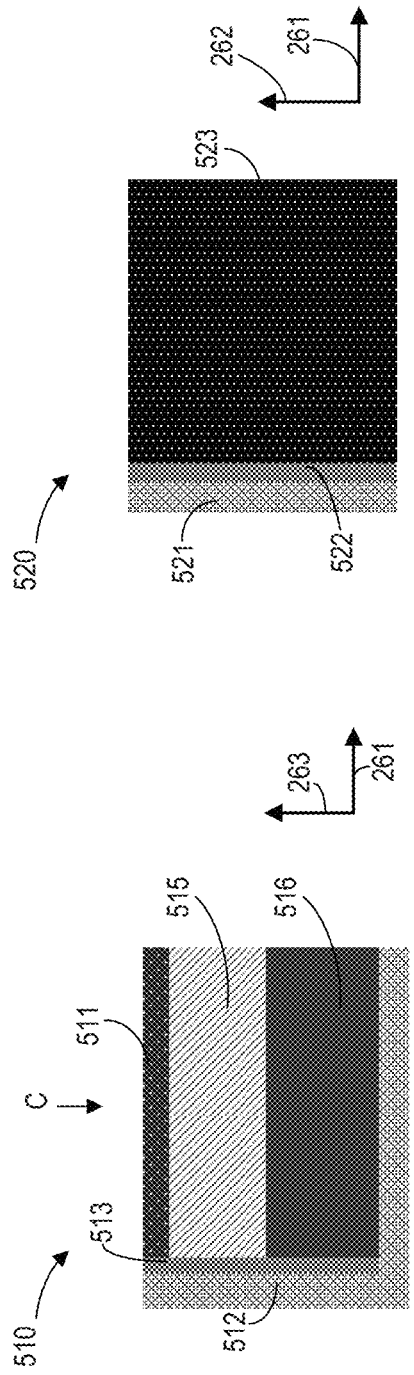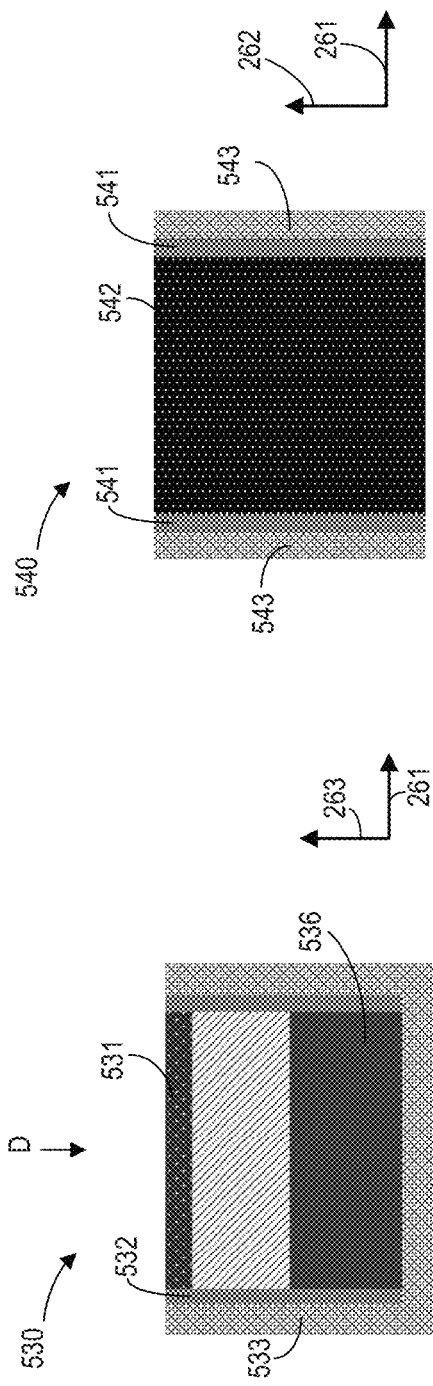
FIG. 5A
FIG. 5B

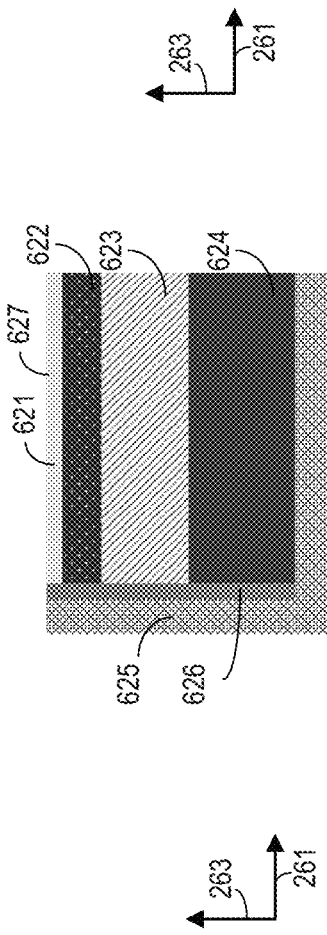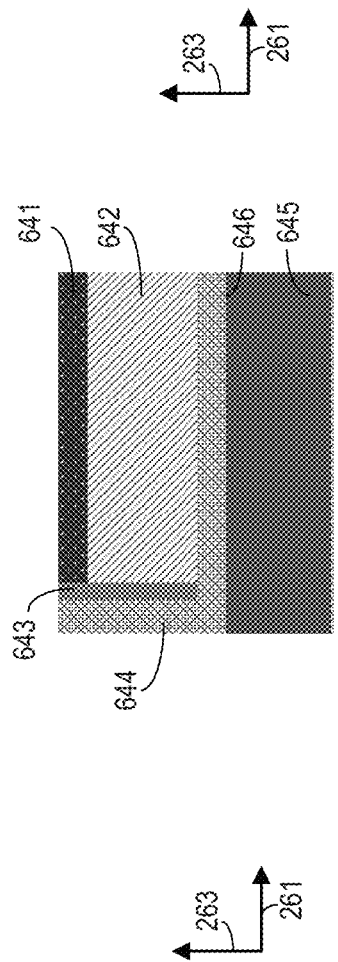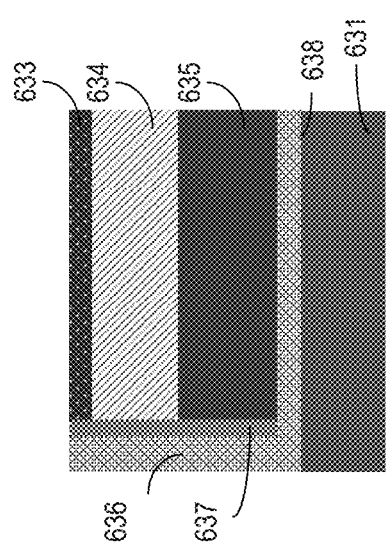

ULTRASOUND TRANSDUCER AND METHOD FOR WAFER LEVEL FRONT FACE ATTACHMENT

CROSS-REFERENCE TO RELATED APPLICATIONS

This application is a divisional of U.S. patent application Ser. No. 15/385,620, entitled "ULTRASOUND TRANSDUCER AND METHOD FOR WAFER LEVEL FRONT FACE ATTACHMENT," and filed on Dec. 20, 2016. The entirety of the above-identified application is hereby incorporated by reference for all purposes.

FIELD

Embodiments of the subject matter disclosed herein relate to an ultrasound transducer, and more particularly, to a single element transducer with wafer level packaging.

BACKGROUND

Single element transducers can be mounted to one end of a probe for invasive imaging of blood vessels or cavities within the human body. By sending a voltage signal to the transducer through the probe, a piezoelectric material within the transducer is excited and generates acoustic signals propagating within the same plane of the excitation. The same piezoelectric material can also convert received acoustic signals into voltage signals. By rotating the probe along its longitudinal axis, a side-looking transducer can image a plane perpendicular to the longitudinal axis of the probe. The side-looking probe can be used in applications such as intravascular imaging. The signal element transducer may alternatively be mounted to one end of the probe to form a forward looking probe, that is, a probe for imaging in the same direction as the longitudinal axis of the cable. The forward looking probe can be used in applications such as rectal imaging. Multiple single element transducers may also be assembled into a sparse array (such as a basket type array) for applications such as mapping a heart chamber. Since the ultrasound probes are designed for invasive imaging, miniaturized ultrasound transducers may be utilized.

Wiring two electrodes of a single element transducer to the probe can be challenging due to the small size of the transducer. One approach is to attach the first electrode of the transducer to a substrate having a printed circuit, and manually apply silver epoxy to connect the second electrode to the substrate. However, this process lacks reproducibility and robustness. Since silver epoxy has high viscosity, therefore it is difficult to manually apply a controlled amount of epoxy. Silver epoxy also lacks robust adhesion to the substrate due to its high sensitivity to moisture and long curing time. Further, due to long touch time and cycle time, the process is not suitable for manufacturing disposable probes.

BRIEF DESCRIPTION

In one embodiment, an ultrasound transducer comprises a piezoelectric layer extending horizontally and laterally, a matching layer extending horizontally and laterally for acoustic impedance matching, and a base package. One surface of the matching layer is electrically coupled to a top surface of the piezoelectric layer and another surface of the matching layer forms a signal pad within a front face of the transducer. The base package is electrically coupled to a bottom surface of the piezoelectric layer, and the base package extends horizontally and laterally to form a back face parallel to the front face, and further extends vertically relative to the back face to form a ground pad within the front face of the ultrasound transducer. In this way, two electrodes (the ground pad and the signal pad) of the transducer are integrated into the transducer body with wafer level packaging, enabling automatic and reliable surface mounting of the transducer onto a substrate.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5A shows one embodiment of a rectangular transducer.

FIG. 5B shows another embodiment of the rectangular transducer.

FIG. 6A shows one embodiment of the single element ultrasound transducer with a dematching layer.

FIG. 6B shows one embodiment of the single element transducer with a second matching layer.

FIG. 6C shows one embodiment of the single element transducer with a second backing layer.

FIG. 6D shows one embodiment of the single element transducer with a piezoelectric layer in contact with a base package.

DETAILED DESCRIPTION

Figure 1:
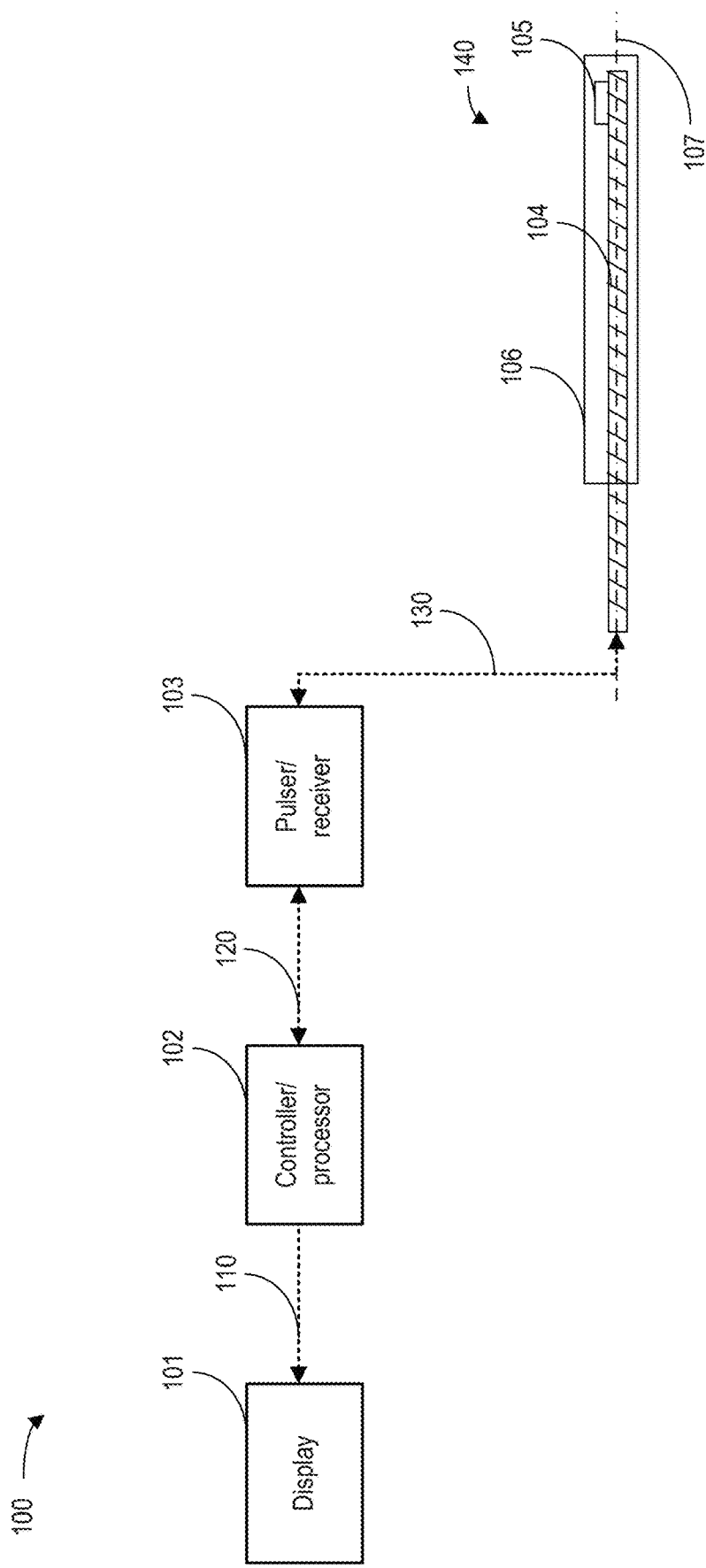
FIG. 1 shows an example ultrasound system attached to a probe including a single element ultrasound transducer.
Figure 2:
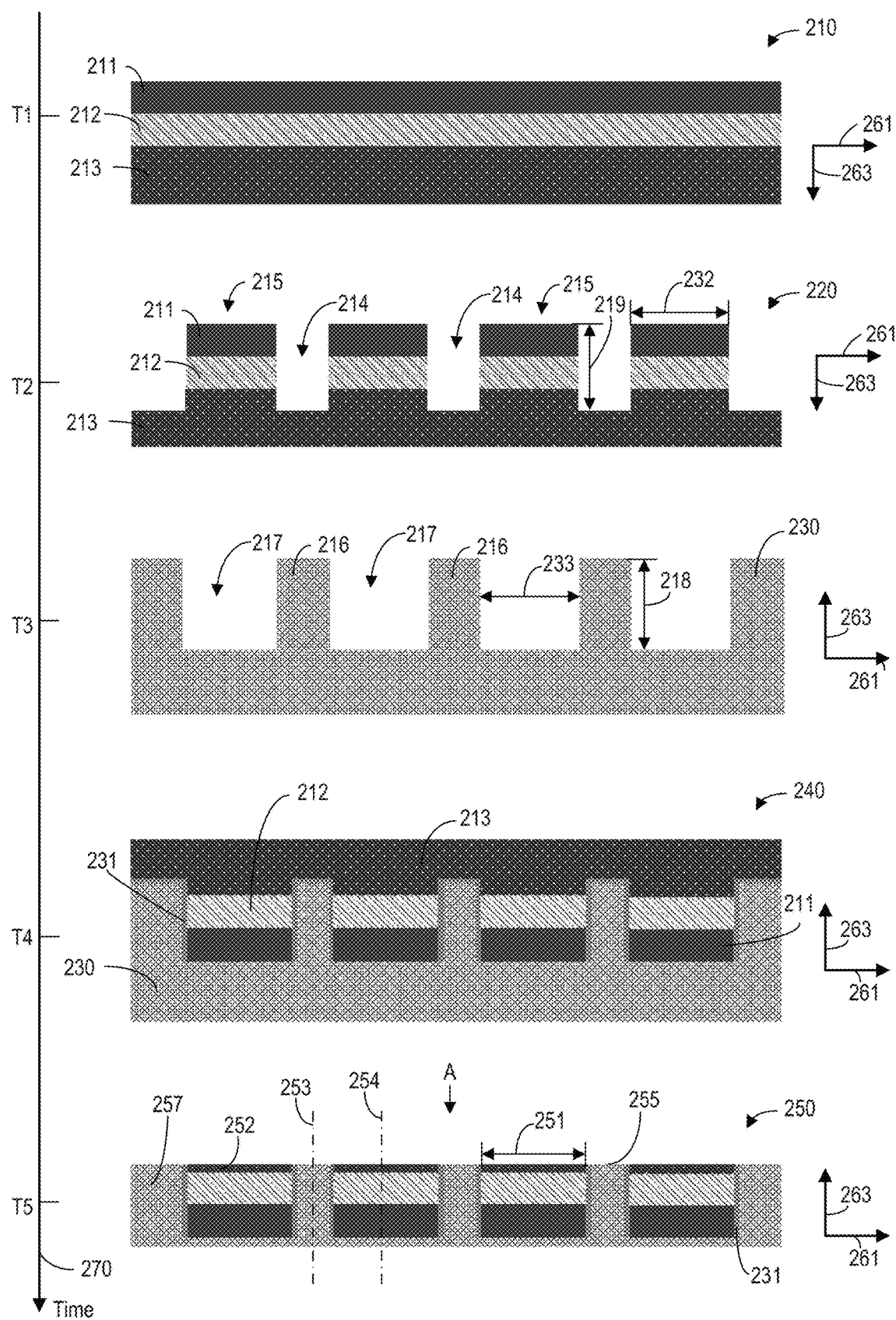
FIG. 2 illustrates an example process of manufacturing an acoustic stack with interdigitated comb structures.
Figure 3:
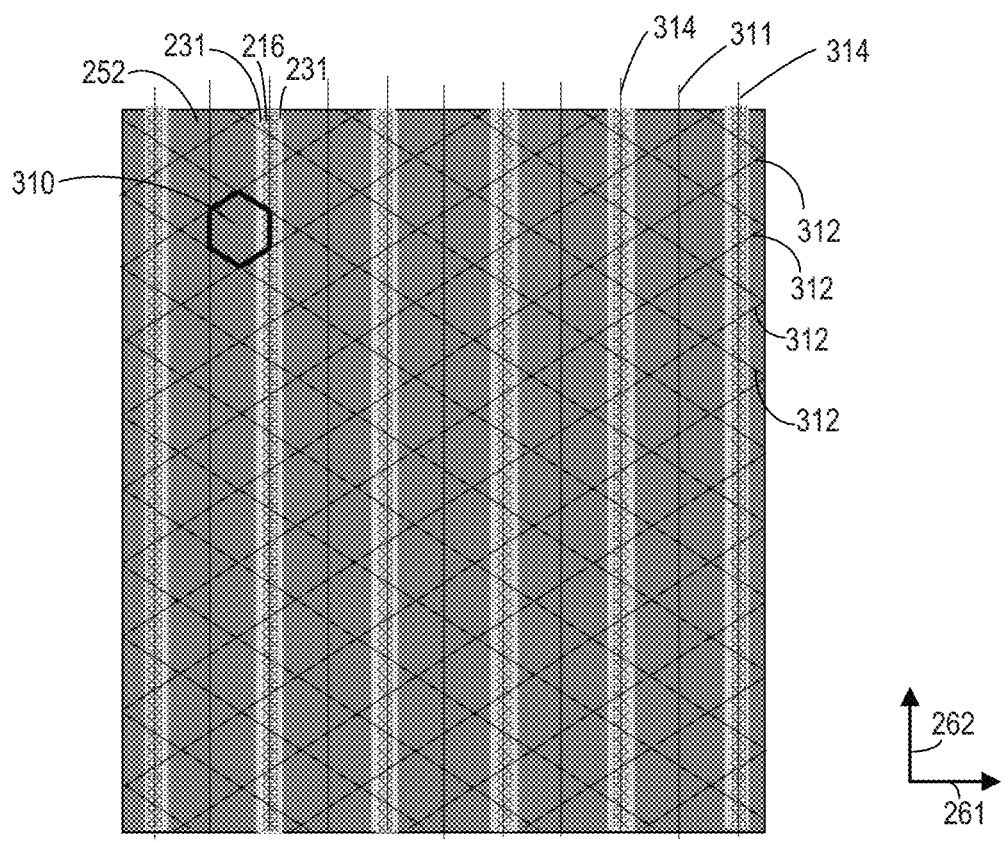
FIG. 3 shows an example pattern for dicing the acoustic stack into a hexagonal transducer.
Figure 4A:
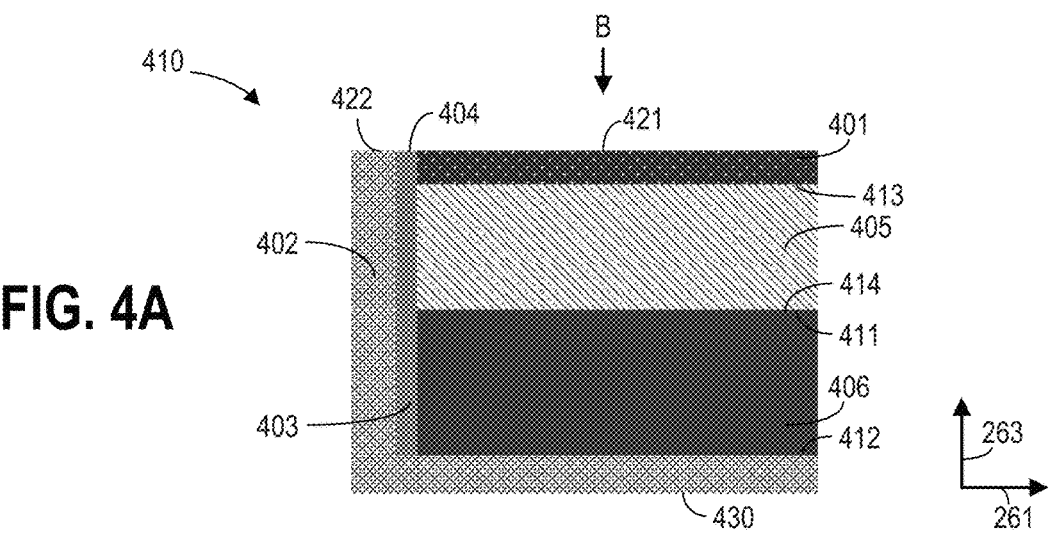
FIG. 4A shows a cross-sectional view of an example embodiment of the hexagonal transducer.
Figure 4B:
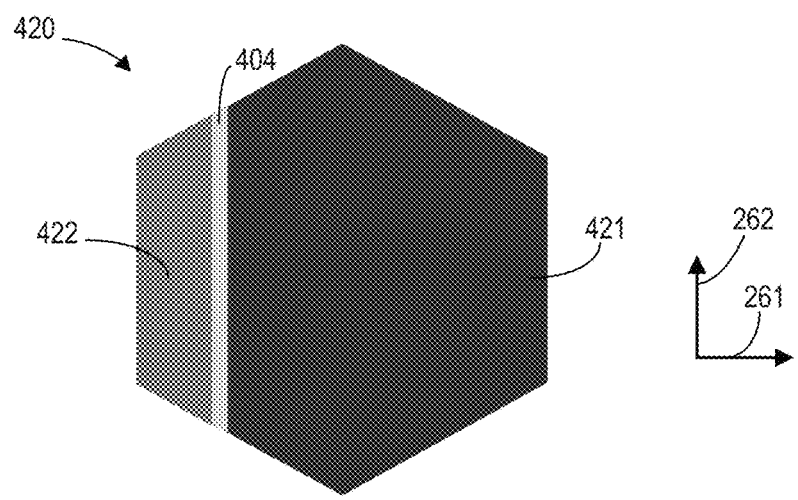
FIG. 4B shows a top view of the hexagonal transducer
Figure 4C:
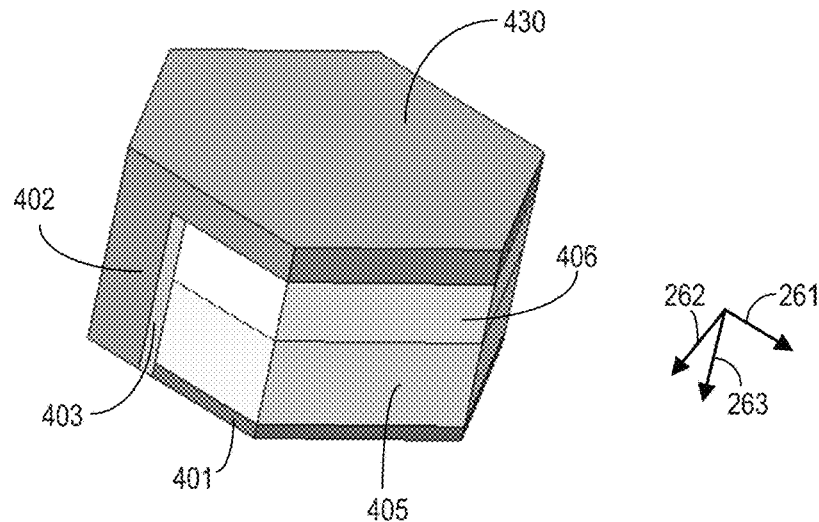
FIG. 4C shows a three dimensional rendering of the hexagonal transducer.
Figure 8:
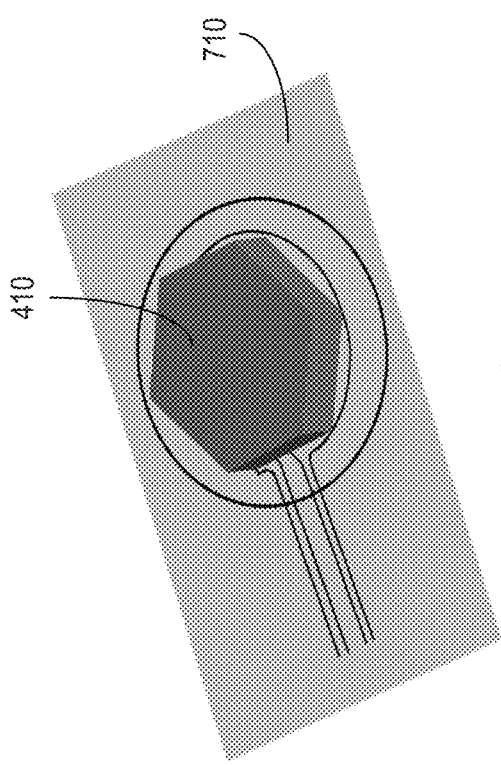
FIG. 8 is a three dimensional rendering of the hexagonal transducer mounted to the substrate.
Figure 9:
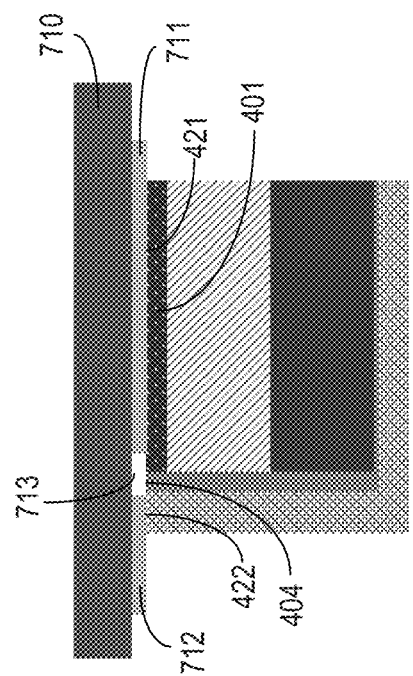
FIG. 9 shows a cross-sectional view of the hexagonal transducer mounted to the substrate.
Figure 7:
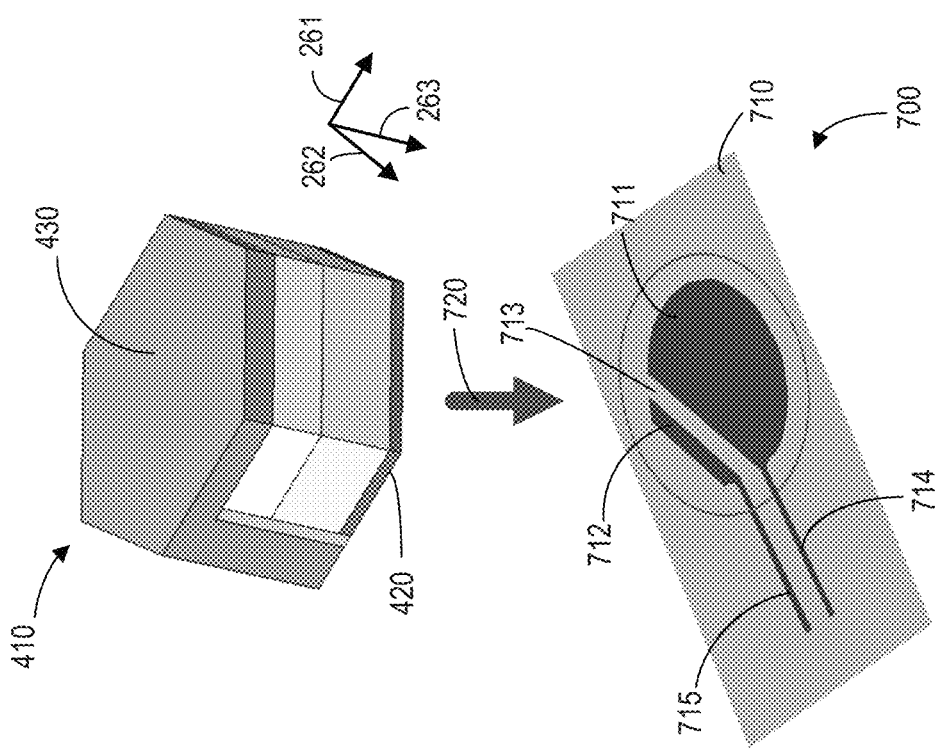
FIG. 7 illustrates an example process for mounting the hexagonal transducer to substrate.
Figure 10A:
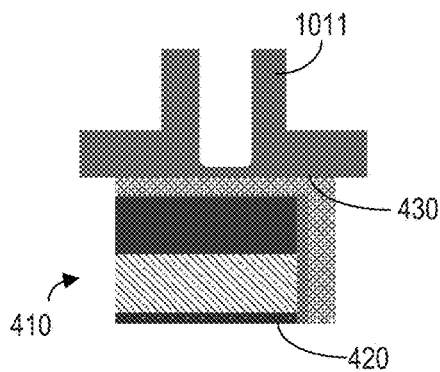
FIG. 10A shows the transducer being picked up by a die ejector.
Figure 10B:
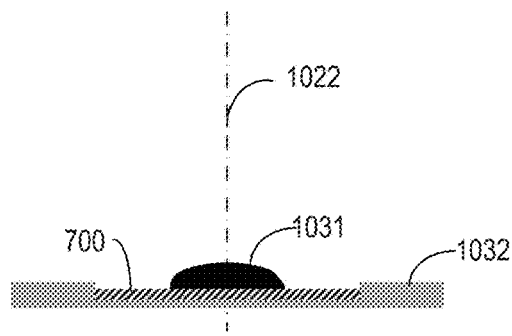
FIG. 10B shows glue dispensed to the substrate.
Figure 10C:
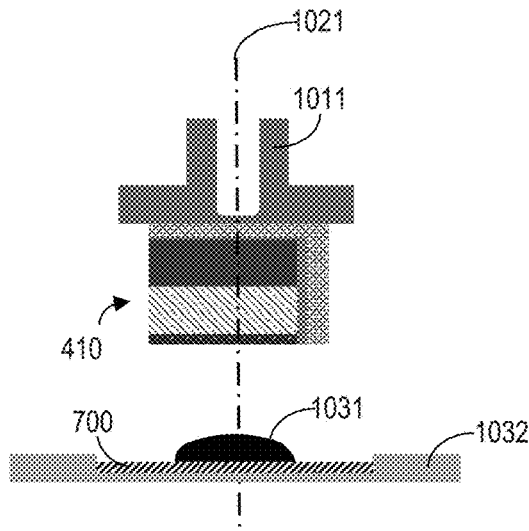
FIG. 10C shows the transducer aligned with the substrate.
Figure 10D:
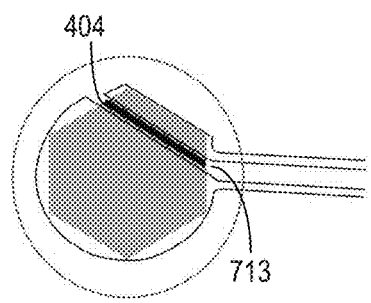
FIG. 10D shows the position of the transducer relative to a circuit printed on the substrate.
Figure 10E:
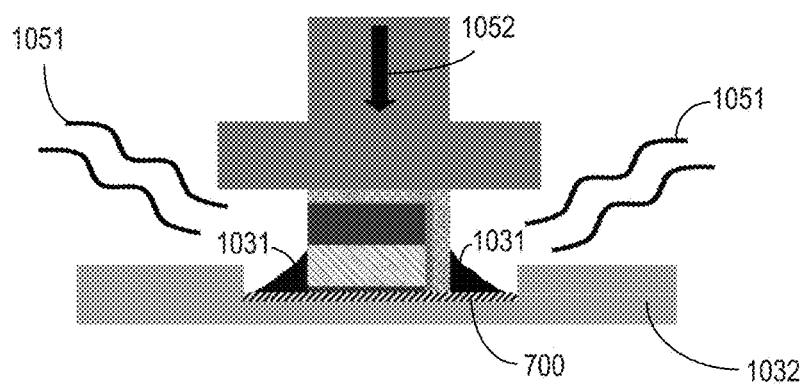
FIG. 10E illustrates the transducer being attached to the substrate.
Figure 11:
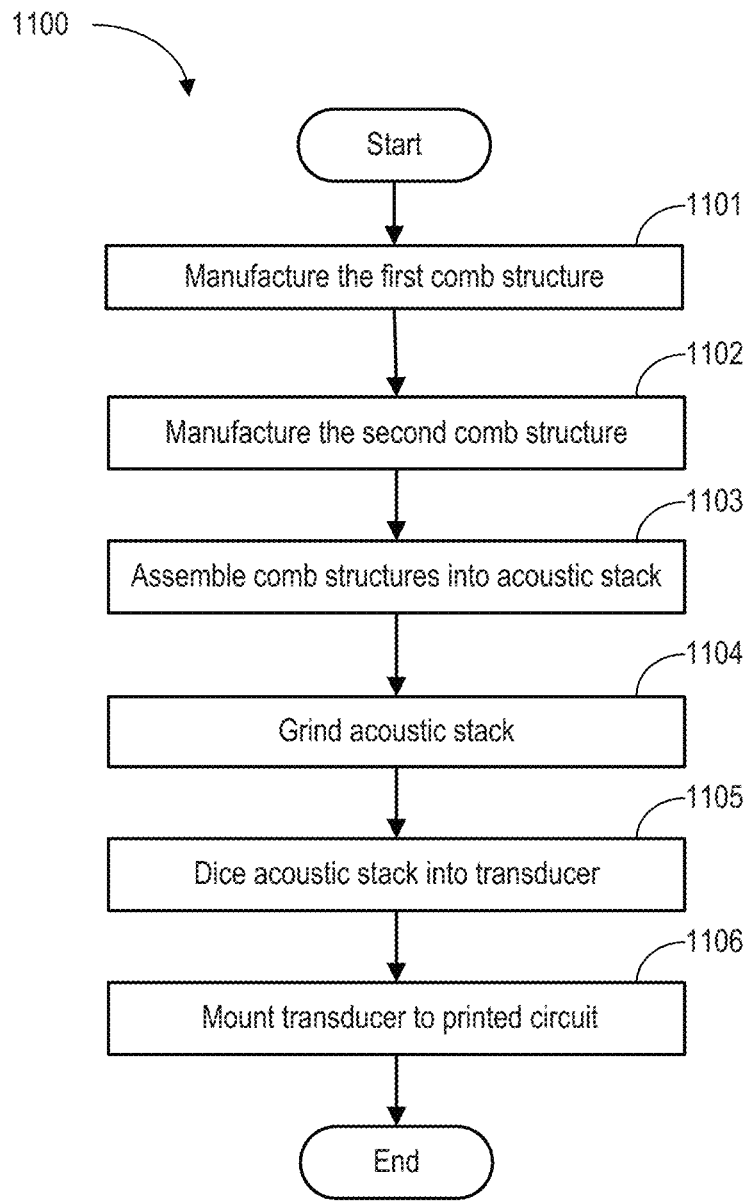
FIG. 11 shows an example method of manufacturing an ultrasound transducer assembly including the single element ultrasound transducer.
Figure 12:
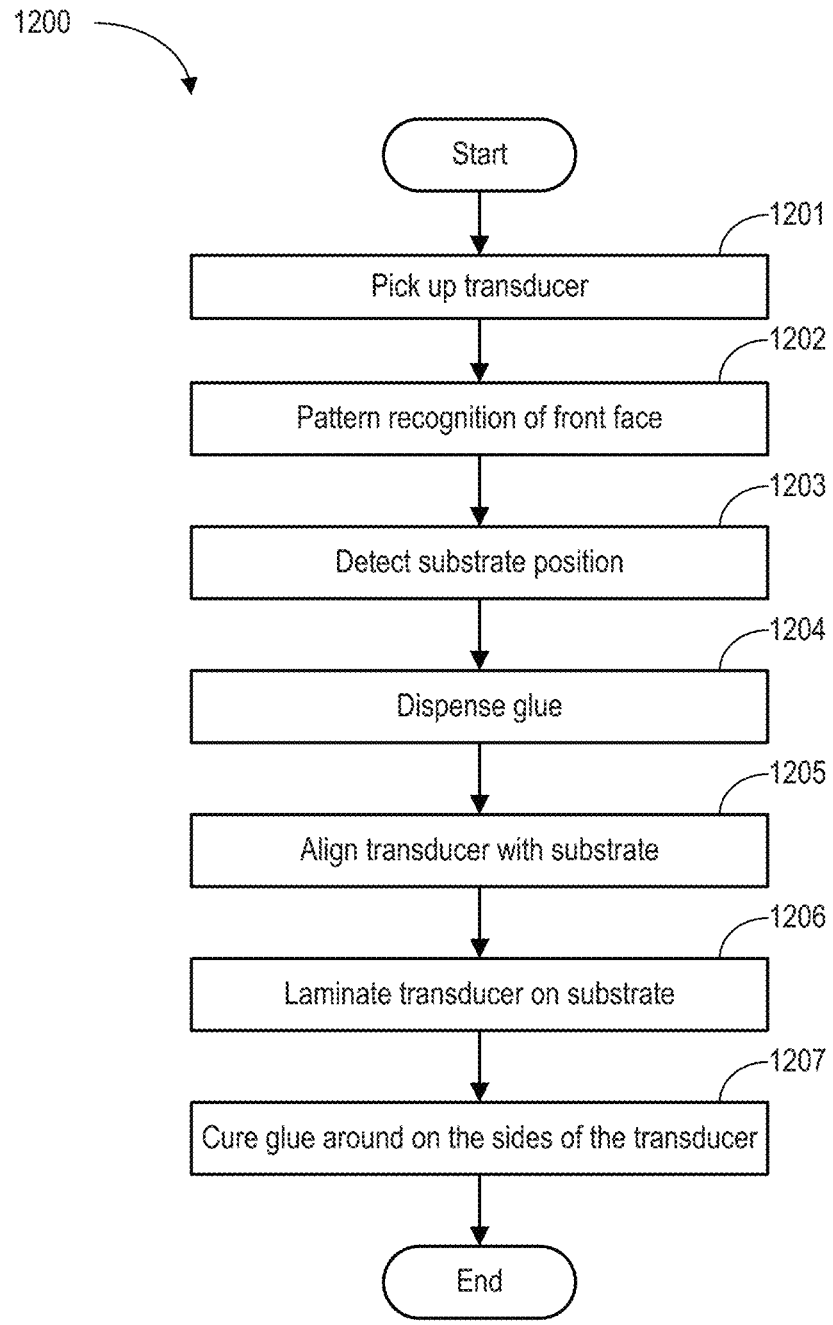
FIG. 12 shows an example method of mounting the transducer to a substrate.

The following description relates to various embodiments of a single element ultrasound transducer. In particular, systems and methods are provided for a single element ultrasound transducer with a wafer level front face attachment for constructing a side-looking, forward-looking, or sparse array ultrasound probe. FIG. 1 shows an example configuration of the side-looking probe attached to an ultrasound imaging system. The single element ultrasound transducer is manufactured through wafer level packaging, by dicing through an acoustic stack including a piezoelectric layer. The procedure of manufacturing the acoustic stack is shown in FIG. 2. The acoustic stack is made by interdigitating two comb structures. FIG. 3 shows an example of dicing pattern for manufacturing a hexagonal transducer. The detailed configuration of the hexagonal transducer is shown in FIGS. 4A-4C. FIGS. 5A and 5B show example embodiments of a rectangular single element transducer. FIGS. 6A-6D show alternative configurations of the single element transducer. Since the two electrodes are integrated into a flat surface, the front face of the transducer may be directly mounted to a substrate with a printed circuit. FIGS. 7-8 show a hexagonal transducer attached to the substrate. FIG. 9 is a cross-sectional view of ultrasound transducer assembled with the substrate. FIGS. 10A-10E illustrate the procedure of assembling the transducer with the substrate. FIG. 11 and FIG. 12 are flow charts showing the method of manufacturing the transducer and the method of mounting the transducer to the substrate. Through the following description of the images, same parts are provided with same reference numerals.

Though a probe with a single element transducer is described by way of example, it should be understood that the present techniques may also be useful for constructing a probe with an array of single element transducers, such as constructing an array based intravascular ultrasound catheter.

FIG. 1 is a schematic diagram of an ultrasound imaging system 100 in accordance with an embodiment of the invention. System 100 includes a display module 101, a controller/processor 102, a pulser/receiver 103, and a probe 140. The dashed lines (110, 120, and 130) indicate communication of electrical signals between system components. The probe includes a cable 104 and a single element ultrasound transducer 105 mounted on one distal end of cable 104. In one embodiment, the transducer faces sideways from cable 104. The transducer generates acoustic signals and receives reflected acoustic signals in a direction perpendicular to the longitudinal axis 107 of the probe. The cable 104 may be a coaxial cable that can rotate relative to its longitudinal axis so that a plane perpendicular to the longitudinal axis of the probe may be imaged (e.g., the cable may have a rotational axis that is parallel to and aligned with the longitudinal axis of the probe). In another embodiment, the transducer may generate acoustic signal along the longitudinal axis 107 of the probe, as a forward looking transducer. In yet another embodiment, multiple transducers may be mounted to the distal end of cable 104 to form an array, such as a basket type array. Probe 140 may further include a sheet 106 covering the cable 104 and the transducer 105. The sheet may be flexible and transparent to acoustic signals.

Pulser/receiver 103 is controlled by controller/processor 102 for generating a high voltage pulse to probe 140. Acoustic signals reflected to the probe from the imaged object are converted into electrical signals and transmitted back to the pulser/receiver. The pulser/receiver may also amplify the received electrical signals from the probe. The received electrical signals are further transmitted to controller/processor 102 via 120. An image or map of the imaged object is constructed based on the received electrical signals and displayed on display 101 and/or stored in memory.

In another embodiment, the probe may include an array of ultrasound transducers, and can image or sense a plane or a volume without rotating cable 104.

The single element ultrasound transducer may be manufactured via wafer level packaging by dicing an interdigitated acoustic stack. FIG. 2 illustrates an example procedure for manufacturing the interdigitated acoustic stack. Arrow 261 denotes a horizontal direction. Arrow 263 denotes a vertical direction, perpendicular to the horizontal direction. The lateral direction is perpendicular to both the horizontal and vertical directions. Axis 270 denotes time and is increasing as indicated by the arrow.

At T1, a layered stack 210 is manufactured. Layered stack 210 comprises a backing layer 211, a piezoelectric layer 212, and a matching layer 213. The layered stack expands horizontally and laterally in a plane. Backing layer 211 and matching layer 213 are mounted vertically relative to the plane of the layered stack, with the piezoelectric layer 212 positioned between the backing layer and the matching layer. A first surface of the piezoelectric layer is in contact with the backing layer. A second surface of the piezoelectric layer, opposite to the first surface, is in contact with the matching layer. The piezoelectric layer maybe bonded with the backing layer and the matching layer with glue such as epoxy.

The piezoelectric layer may be made with a piezoelectric material, such as lead zirconate titanate. The thickness of the piezoelectric layer may be half of the wavelength of the acoustic signal. The first surface and the second surface of the piezoelectric layer act as two electrodes. By applying a voltage across the two electrodes, the piezoelectric material is excited and generates acoustic signals in a direction parallel to the vertical direction. The piezoelectric material may also convert acoustic signals back into electrical signals across the two electrodes. When the piezoelectric material is switched from the transmission to the receiving mode, ringing effect may occur and affect the received signal. The backing layer can dampen the ringing effect. The backing layer may be made of conductive material such as graphite or aluminum. The matching layer is for matching the acoustic impedance difference between the transducer and the medium that the transducer is immersed within during imaging. As an example, the matching layer may be configured to match the acoustic impedance difference between the transducer and water when the transducer is used for biological tissue imaging. The matching layer may be made of conductive material such as silver epoxy, graphite, or aluminum. As an example, the thickness of the matching layer may be one fourth of the wavelength of the acoustic signal. As another example, the thickness of the backing layer may be determined based on a required acoustic attenuation.

At T2, a first comb structure 220 is made. The first comb structure may be manufactured by dicing evenly spaced kerfs 214 on the layered structure 210. The kerfs extend along the lateral direction, and are evenly spaced along the horizontal direction. Kerf 214 extends vertically through the backing layer 211 and the piezoelectric layer 212. Kerf 214 further extends into, but not through the matching layer 213. As such, fins 215 are formed in the lateral direction. The adjacent fins are separated by a kerf.

At T3, a conductive base package 230 is made. The base package 230 is a comb structure complimentary to the first comb structure 220. The base package may be manufactured by dicing kerfs into a flat conductive substrate. The base package may made from conductive material include graphite, porous graphite filled with resin, stainless steel, or aluminum. The base package includes fins 216 extending laterally and are separated by kerfs 217. The base package is complimentary to the first comb structure 220 in a way that a respective depth 218 of each of the fins of the base package 230 is the same as a respective depth 219 of each of the fins of the first comb structure 220, and a respective width 232 of each fin of the first comb structure 220 is less than a respective width 233 of each kerf in the base package 230. In other words, in both the first comb structure and the base package, the depth of the kerfs may be the same as the height of the fins, and the width of the fins of the first comb structure is less than the width of the kerfs of the base package. As such, the base package 230 and the first comb structure 220 can be laminated into an acoustic stack with interdigitated comb structures.

At T4, acoustic stack 240 is made by laminating the first comb structure 220 and the base package 230. Non-conductive glue 231 is dispensed between the fins of the first comb structure 220 and the fins of the base package 230. As such, piezoelectric layer 212 and backing layer 211 are insulated from the base package 230 by the non-conductive glue. As an example, the non-conductive glue may be a non-conductive resin such as epoxy.

At T5, excessive material in the matching layer is removed. In another embodiment, material in both the matching and the backing layers of the acoustic stack 240 is removed. As an example, the excessive material may be removed by grinding. The matching layer is ground so that the width 251 of the ground matching layer 252 is the same as the width 232 of the fin in the first comb structure. The top surface of the ground acoustic stack includes the top surface 255 of the fin of the conductive base package. As such, viewing from direction A, the matching layer and the fins of the base package are separated by non-conductive glue. 253 and 254 indicate the central axes of the fin of a base package 257 and the fin of the first comb structure, respectively. The top surface of the matching layers are separated by the top surface 255 of fins. The base package forms the bottom surface of acoustic stack 250. A top view of the acoustic stack 250 viewed from direction A is shown in FIG. 3. As appreciated by FIG. 3, the top surface of acoustic stack 250 comprises alternating sections of base package (e.g., fin 216) and matching layer 252 separated by non-conductive glue 231.

FIG. 3 shows an example pattern of dicing the ground acoustic stack 250 into individual ultrasound transducers. Arrow 262 denotes the lateral direction, and arrow 261 denotes the horizontal direction. The individual transducers may be of various shapes based on the application and physical constrains of the probe. As a non-limiting example, a dicing pattern for hexagonal transducers is shown here. The acoustic stack may be diced along lateral lines 311 and 314, and diagonal lines 312. Lateral lines 314 may be along the fins 216 of the base package. As an example, line 314 is the central axis of the fin of the base package (253 in FIG. 2). Lateral lines 311 may be between the two lateral lines 314 and may be along the ground matching layer 252. As an example, line 311 is the central axis of the fin of the first comb structure (254 in FIG. 2). Thus, when the acoustic stack 250 is diced as shown, lateral slices along the fins of the base package and along the matching layer are made. The fins of the base package extend along the entirety of the depth of the acoustic stack from the top surface of the acoustic stack viewed in FIG. 3 to a bottom surface of the acoustic stack opposite the top surface. The matching layer does not extend along the entirety of the depth of the acoustic stack, but rather the piezoelectric layer, backing layer, and base package are positioned under the matching layer. As such, the front face of an individual transducer 310 includes a ground pad formed by the base package and a signal pad formed by the matching layer and separated from the ground pad formed by the non-conductive glue. The example dicing pattern has the advantage of obtaining a transducer with near round top surface with minimal waste of the material.

In another embodiment, rectangular transducers with rectangular front faces and at least one ground pad in the front face may be made by dicing along lateral lines and horizontal lines. At least one lateral line is along the fin of the base package to ensure the front face of the transducer has a ground pad.

FIGS. 4A-4C show an example hexagonal single element ultrasound transducer that may be formed by dicing the acoustic stack 250 of FIG. 2, for example. Arrow 263 denotes the vertical direction, arrow 261 denotes the horizontal direction, and arrow 262 denotes the lateral direction.

FIG. 4A is a side view of transducer 410. The transducer comprises a flat front surface including a signal pad 421 and a ground pad 422. The signal pad 421 is a surface of and hence formed by the matching layer 401 and is electrically coupled to a top surface 413 of the piezoelectric layer via the matching layer. The ground pad 422 is a surface of and hence formed by the base package 402 and is electrically coupled to a bottom surface 414 of the piezoelectric layer via the base package 402 and the backing layer 406. By applying a voltage across the two electrodes of the transducer (that is, the signal and ground pad), a voltage potential is built between the top and bottom surfaces of the piezoelectric layer. As such, the piezoelectric layer 405 may be excited and generates an acoustic signal. Note that the two electrodes of the transducer are interchangeable. When applying a voltage across the electrodes, the high voltage may be supplied to either the ground pad or the signal pad. The configuration of the transducer enables the front surface to be easily mounted to a substrate having a printed circuit. Meanwhile, since the electrodes of the transducer are manufactured through wafer level packaging, the transducer is one compact component, therefore can reliably and robustly generate and receive acoustic signals.

The single element transducer comprises a vertically stacked matching layer 401, piezoelectric layer 405, and backing layer 406, wherein the piezoelectric layer is between the matching layer and the backing layer. The width and length of the matching layer, piezoelectric layer, and the backing layer along the horizontal and lateral directions are the same. The top surface 411 of the backing layer is in direct contact with bottom surface 414 of the piezoelectric layer. The top surface 413 of the piezoelectric layer is in direct contact with the matching layer 401. The bottom surface 412 of the backing layer is in direct contact with base package 402. Base package 402 extends horizontally and laterally and forms a back face 430 of the transducer. The back face 430 is a flat surface. Base package 402 extends vertically from the back face 430 to the front face of the transducer, and forms a ground pad 422 within the front face. The front face also includes a signal pad 421 formed by the top surface of matching layer 401. The ground pad 422 and the signal pad 421 are separated by a non-conductive groove 404. The non-conductive groove is the top surface of non-conductive glue 403. The non-conductive glue extends vertically and separates the matching layer 401 and the piezoelectric layer 405 from the base package 402. The non-conductive glue 403 also separates the side surface of backing layer 406 from base package 402.

Herein, a top surface of a layer refers to a flat surface extending horizontally and laterally, and is higher than a bottom surface, wherein the increased height in the vertical direction is indicated by arrow 263. The side of a layer refers to a side surface of the layer parallel to the vertical axis.

In another embodiment, backing layer 406 may be replaced with a dematching layer. The dematching layer may be constructed with a material of higher acoustic impedance than the piezoelectric layer so that the majority of acoustic energy is transmitted through the matching layer.

FIG. 4B shows the front face 420 of the hexagonal transducer, viewing from a direction B shown in FIG. 4A. The front face is a flat surface including ground pad 422, signal pad 421, and non-conductive groove 404 electrically separating and insulating the ground pad from the signal pad.

FIG. 4C is a three dimensional view of the hexagonal transducer. Base package 402 partially surrounds a stack including the backing layer 406, the piezoelectric layer 405, and the matching layer 401.

FIGS. 5A and 5B show a cross-sectional view and a top view, respectively, of a rectangular single element ultrasound transducer in two embodiments. The rectangular transducers may be manufactured by dicing an acoustic stack, such as the acoustic stack 250 in FIG. 2, with horizontal and lateral dicing trajectories. Arrow 263 denotes the vertical direction, arrow 261 denotes the horizontal direction, and arrow 262 denotes the lateral direction.

FIG. 5A shows one embodiment of the rectangular transducer. In a cross-sectional view 510 of the transducer, the transducer comprises matching layer 511, piezoelectric layer 515, backing layer 516, base package 512, and non-conductive glue 513. The base package partially surrounds the piezoelectric layer, backing layer, and backing layer. The non-conductive glue separates the base package from the piezoelectric layer. The front face 520 of the rectangular transducer viewed from direction C includes the ground pad 521, signal pad 523, and non-conductive groove 522 separating the ground pad and the signal pad. The ground pad 521, non-conductive groove 522, and signal pad 523 are all rectangular.

The rectangular transducers may be manufactured by dicing the acoustic stack 250 in FIG. 2 with horizontal and lateral dicing lines, wherein the lateral dicing lines including lines along the fins of the base package and lines along the fins of the first comb structure (such as 314 and 311 of FIG. 3).

FIG. 5B shows another embodiment of the rectangular transducer having two ground pads within the front face. The additional ground pad may serve as a redundancy to ensure reliable grounding of the transducer. The cross-sectional view of the transducer is shown as 530, and the front face of the transducer view from direction D is shown as 540. The matching layer 531, piezoelectric layer 535, and backing layer 536 form a layered structure. The top surface of matching layer forms signal pad 542 within the front face of the transducer. Base package 533 is in contact with backing layer 536, and extends laterally and horizontally to form the back face 531 of the transducer. The base package extends vertically from the back face and forms the two ground pads 543 within the front face 540. Non-conductive glue 532 extend vertically between the layered stack and the base package, and form two non-conductive grooves 541 within the front face. Within the front face, the two ground pads 543 locate on opposite sides of the signal pad 542. The signal pad is insulated from the ground pad by the non-conductive groove 541.

As an example, the rectangular transducers may be manufactured by dicing the acoustic stack 250 in FIG. 2 with horizontal and lateral dicing lines, wherein the lateral dicing lines are along the fins of the base package (such as 314 of FIG. 3). Further, at least in one example, the width of the fins and kerfs of both the first comb structure and base package may be adjusted in order to adjust the width of the transducer along the horizontal axis. For example, the width of fins of the first comb structure and the width of kerfs of the base package are decreased to reduce the width of the rectangular transducer with two ground pads along the horizontal direction. In this way, a transducer having two ground pads may be produced, where the dimensions of the signal pad may be the same as a transducer having a single ground pad.

FIGS. 6A-6D show cross-sectional views of other embodiments of the transducer. FIG. 6A shows a first embodiment of the transducer with a dematching layer. FIG. 6B shows a second embodiment of the transducer with a second matching layer. FIG. 6C shows a third embodiment of the transducer with a second backing layer. FIG. 6D shows a fourth embodiment of the transducer with a piezoelectric layer in contact with a base package.

In FIG. 6A, dematching layer 611 is added between the piezoelectric layer 613 and backing layer 614. The dematching layer is of the same width and length in the horizontal and lateral directions as the piezoelectric layer, and is separated from base package 615 by non-conductive glue 616. The dematching layer may reduce the thickness of the piezoelectric layer 613 to a quarter acoustic wavelength, and also reduce the thickness of the backing layer. As an example, the dematching layer may be made with tungsten carbide, and may be of a quarter of acoustic wavelength thick.

In FIG. 6B, a second matching layer 621 may be added on top of the first matching layer 622 to provide improved impedance matching between the piezoelectric layer and the imaging medium. The second matching layer is of the same width and length in the horizontal and lateral directions as the piezoelectric layer 623 and the backing layer 624. The signal pad 627 within the front face of the transducer is the top surface of the second matching layer. The second matching layer 621 is separated from the base package 625 by non-conductive glue 626.

In FIG. 6C, a second backing layer 631 is added. The base package 636 partially surrounds a stack including a matching layer 633, a piezoelectric layer 634, and a first backing layer 635. The top surface 638 of the second backing layer is in contact with the back face 638 of the transducer. The second backing layer 631 extends horizontally and laterally, and is separated from the first backing layer 635 by the base package 636. The second backing layer may provide extra dampening of the ringing effect caused by exciting the piezoelectric layer. The second backing layer may be made of either conductive or non-conductive material.

In FIG. 6D, instead of having a backing layer between a piezoelectric layer and a base package, the piezoelectric layer 642 may be in direct contact with the base package

644. The matching layer 641 is on top of the piezoelectric layer 642. The matching layer 641 is separated from the base package 644 by non-conductive glue 643. The backing layer 645 is in direct contact with the back face 646 of the transducer. The backing layer 645 may be either electrically conductive or non-conductive. For example, the backing layer 645 may be constructed out of non-conductive material such as epoxy glue mixed with higher impedance loads like tungsten powder or aluminum oxide, or epoxy glue mixed with low impedance material such as hollow micro balloon of polymer.

FIG. 7 illustrates a single element ultrasound transducer being mounted to substrate 700 as shown by arrow 720. As a non-limiting example, a hexagonal transducer 410 is shown in the figure. The substrate may be a flex pad with circuit printed on top. As an example, the flex pad may be polyimide. The circuit may be printed on the flex pad with copper. The printed circuit includes a ground pad 712, a signal pad 711, and a separation line 713 separating the ground pad from the signal pad. The printed circuit further includes a ground wire 715 connected to the ground pad 712, and a signal wire 714 connected to the signal pad 711. The ground wire and signal wire may be housed in a coaxial cable, at least in one example. The ground and signal wires may be coupled to the probe for transmitting electrical signals. The ground pad 712 and the signal pad 711 may be coupled to the coaxial cable of the probe. The front face 420 of the transducer is mounted to the printed circuit on flex pad 710, with the ground pad of the transducer aligned with ground pad 712 on the flex pad, the signal pad of the transducer aligned with signal pad 711 on the flex pad, and the non-conductive groove of the transducer aligned with the separation line 713 on the flex pad.

FIG. 8 is a three dimensional view of a hexagonal transducer attached to flex pad 710. FIG. 9 shows a cross-sectional view showing the transducer with its front face in contact with the printed circuit. Specifically, signal pad 421 of the transducer is in contact with signal pad 711 of the printed circuit; ground pad 422 of the transducer is in contact with ground pad 712 of the printed circuit; and non-conductive groove 404 is aligned with separation line 713. As an example, the ground pad and signal pad on flex pad 710 may be printed by depositing copper onto a polyimide layer. The copper layer of the printed circuit and matching layer 401 of the acoustic stack may act as a mass of a spring-mass object, with the matching layer corresponding to the spring. The respective acoustic impedance and the thickness of the mass (the copper of the flex) and the spring (the matching layer) can be adjusted in such a way that the resonant frequency of the mass-spring object falls into the range of preferred bandwidth for specific application. The polyimide of the flex pad may act as a final matching layer.

In the above embodiments of the single element transducer, the signal pad is electrically coupled to the top layer of the piezoelectric layer, and the ground pad is electrically coupled to the bottom layer of the piezoelectric layer. To generate an acoustic signal, a voltage potential may be applied to the transducer by electrically coupling a positive tab of a power source to the signal pad, and a negative (or ground) tab of the power source to the ground pad of the transducer. Alternatively, a voltage potential may be applied to the transducer by electrically coupling a positive tab of the power source to the ground pad of the transducer, and the negative tab (or ground) tab of the power source to the signal pad of the transducer. In other words, the signal and ground pad of the transducer are interchangeable.

FIG. 11 shows a high level flow chart of method 1100 for manufacturing a single element transducer assembly, wherein the transducer has a wafer level front face attachment to a flat substrate.

At 1101, a first comb structure is manufactured. As shown in 210 and 220 of FIG. 2, the first comb structure is made by dicing kerfs in a layered structure including a matching layer, a piezoelectric layer, and a backing layer.

At 1102, a base package is manufactured. The based package is in the form of a second comb structure, complimentary to the first comb structure. As shown in 230 of FIG. 2, the base package may be made by dicing kerfs in a conductive material.

At 1103, the first comb structure is laminated with the base package into an acoustic stack as shown in 240 of FIG. 2. Non-conductive glue is dispensed between the first comb structure and the base package to bond the comb structures together.

At 1104, the acoustic stack is ground so that the matching layer is separated from the base package by the non-conductive glue at the top surface of the acoustic stack. The ground acoustic stack is shown in 250 of FIG. 2 and FIG. 3.

At 1105, the ground acoustic stack is diced into individual transducers. The transducer's front face may be of various shapes based on the dicing pattern. As an example, the dicing pattern for a hexagonal transducer is shown in FIG. 3.

At 1106, the individual transducer is mounted onto a flat substrate having a printed circuit. An example of the procedure is shown in FIGS. 10 and 12.

FIG. 12 shows method 1200 for mounting a transducer to a substrate via surface mounting. As an example, the transducer may be mounted to a substrate by a die bonding method. Procedures of method 1200 are illustrated in FIGS. 10A-10E. Method 1200 may be performed in order to mount the hexagonal transducer 410 to substrate 700 of FIG. 7, for example.

At 1201, the transducer is picked up by a die ejector. As shown in FIG. 10A, the transducer 410 is picked up by die ejector 1011. The die ejector 1011 may pick up the transducer by attaching to the back face 430 of the transducer.

At 1202, method 1200 determines the orientation of the transducer by pattern recognizing of its front face 420. As an example, the orientation may be determined by identifying the ground pad and the signal pad within the front face. In some examples, the orientation of the transducer may be determined before the transducer is picked up by the die ejector.

At 1203, method 1200 determines the location of the substrate. As an example, method 1200 may determine the location of the substrate by pattern recognizing the structure of the printed circuit of the substrate. As another example, method 1200 may determine the location of the substrate by identifying the position of the holder holding the substrate, as well as the relative location of the substrate with respect to the holder.

At 1204, glue is dispensed on the printed circuit of the substrate. The glue may be cyanoacrylate glue. As shown in FIG. 10B, glue 1031 is dispensed on to substrate 700 positioned on holder 1032. The glue may be dispensed such that the central axis of the dispensed glue 1022 is aligned with a central axis of the printed circuit.

At 1205, method 1200 aligns the front face of the transducer with the printed circuit of the substrate. For example, as shown in FIG. 10C, the central axis 1021 of the acoustic stack is first aligned with the central axis 1022 of glue. Then, as shown in FIG. 10D, the non-conductive groove 404 of the acoustic stack is aligned with the separation line 713 of the printed circuit by rotating the transducer relative to its central axis 1021. Alternatively, the non-conductive groove 404 of the acoustic stack may be aligned with the separation line 713 by rotating the holder 1032 relative to the central axis of the glue 1022. As such, the signal pad of the transducer is aligned with the signal pad of the printed circuit, and the ground pad of the transducer is aligned with the ground pad of the printed circuit.

At 1206, the transducer is laminated onto the substrate by applying pressure to the transducer. As such, the front face of the transducer is in direct contact with the printed circuit of the substrate. As shown in FIG. 10E, pressure 1052 is applied to the transducer. As a result, the glue 1031 is pushed away from its original dispensed location and becomes peripheral to the transducer.

At 1207, the glue is cured to secure the bonding between the transducer and the substrate. As one example, the glue may be cured by UV light 1051, as shown in FIG. 10E.

A technical effect of the disclosure is that a single element ultrasound transducer is manufactured via wafer level packaging. The transducer includes two electrodes integrated to a flat surface of the transducer. Thus, the transducer is more robust in generating and receiving acoustic signals. Another technical effect of the disclosure is that by arranging the two electrodes within a same flat surface of the transducer, the transducer can be easily and reliably mounted to a flat substrate with printed circuit. Further, this arrangement enabled automatic mounting of the transducer to the substrate.

In one embodiment, an ultrasound transducer comprises a piezoelectric layer, a matching layer for acoustic impedance matching, one surface of the matching layer is electrically coupled to a top surface of the piezoelectric layer and another surface of the matching layer forming a signal pad within a front face of the ultrasound transducer, and a base package electrically coupled to a bottom surface of the piezoelectric layer, the base package extending horizontally and laterally to form a back face of the ultrasound transducer parallel to the front face of the ultrasound transducer, and extending vertically relative to the back face of the ultrasound transducer to form a ground pad within the front face of the ultrasound transducer. In a first example of the embodiment, the base package is electrically conductive, and the ultrasound transducer generates an acoustic signal by coupling a voltage signal across the ground pad and the signal pad. A second example of the embodiment optionally includes the first example and further includes a non-conductive glue extending vertically relative to the piezoelectric layer and separating the base package from the piezoelectric layer. A third example of the embodiment optionally includes one or more of the first and second examples, and further includes, wherein the non-conductive glue forms a non-conductive groove within the front face of the ultrasound transducer. A fourth example of the embodiment optionally includes one or more of the first through third examples, and further includes, wherein the non-conductive groove separates the ground pad from the signal pad. A fifth example of the embodiment optionally includes one or more of the first through fourth examples, and further includes, a conductive backing layer between the piezoelectric layer and the base package. A sixth example of the embodiment optionally includes one or more of the first through fifth examples, and further includes, a dematching layer between the piezoelectric layer and the backing layer. A seventh example of the embodiment optionally includes one or more of the first through sixth examples, and further includes, wherein the backing layer is a first backing layer and further comprising a second backing layer extending horizontally and laterally, with one surface in contact with the base package along the back face of the transducer. An eighth example of the embodiment optionally includes one or more of the first through seventh examples, and further includes, a backing layer in contact with the base package along the back face of the transducer.

In another embodiment, an ultrasound transducer assembly comprises a flat substrate, and an ultrasound transducer having a front face mounted to the flat substrate, the front face comprising: a ground pad electrically coupled to a first surface of a piezoelectric layer, the ground pad formed by a base package, the base package extending vertically from the ground pad to a back face of the ultrasound transducer, a signal pad electrically coupled to a second surface of the piezoelectric layer, the signal pad formed by a matching layer, and a non-conductive groove separating the ground pad and the signal pad. In a first example of the embodiment, the back face of the ultrasound transducer is formed by the base package. A second example of the embodiment optionally includes the first example and further includes, a second ground pad with the front face, wherein the non-conductive groove is formed by a non-conductive glue, and the non-conductive glue extends vertically relative to the front face and separates the base package from the piezoelectric layer. A third example of the embodiment optionally includes one or more of the first and second examples, and further includes, wherein the second ground pad is formed by the base package. A fourth example of the embodiment optionally includes one or more of the first through third examples, and further includes, wherein the flat substrate includes one surface printed with a circuit, and the circuit is electrically coupled to a coaxial cable.

In another embodiment, a method comprises laminating a comb structure and a conductive base package into an acoustic stack with a non-conductive glue, the comb structure comprising a first fin including a piezoelectric layer intermediate a matching layer and a backing layer, the conductive base package comprising a second fin and defining a bottom surface of the acoustic stack; grinding the acoustic stack, a top surface of the ground acoustic stack including a top surface of the second fin of the conductive base package; and dicing the acoustic stack along a plane extending from a top surface of the second fin of the conductive base package to the bottom surface of the acoustic stack and intersecting the second fin, thereby to produce an ultrasound transducer having a flat front face comprising: a ground pad formed by the conductive base package; a signal pad formed by the matching layer, and a non-conductive groove separating the ground pad and the signal pad. In a first example of the embodiment, wherein the non-conductive groove is formed by a non-conductive glue. A second example of the embodiment optionally includes the first example and further includes, manufacturing the comb structure by dicing a layered stack comprising the backing layer, the matching layer, and the piezoelectric layer. A third example of the embodiment optionally includes one or more of the first and second examples, and further includes, the comb structure and the base package are interdigitating laminated. A fourth example of the embodiment optionally includes one or more of the first through third examples, and further includes, mounting the ultrasound transducer to a substrate by aligning the front face of the ultrasound transducer with a circuit printed of the substrate. A fifth example of the embodiment optionally includes one or more of the first through fourth examples, and further includes, wherein the circuit includes a ground pad, a signal pad, and a separation line insulating the ground pad from the signal pad, and aligning the front face with the circuit includes aligning the non-conductive groove of the ultrasound transducer with the separation line.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   laminating a comb structure and a conductive base package into an acoustic stack with a non-conductive glue, the comb structure comprising a first fin including a piezoelectric layer intermediate a matching layer and a backing layer, the conductive base package comprising a second fin that extends laterally from the conductive base package, the conductive base package forming a bottom surface of the acoustic stack;
   grinding the acoustic stack, a top surface of the ground acoustic stack including a top surface of the second fin of the conductive base package; and
   dicing the ground acoustic stack along a plane extending from the top surface of the second fin of the conductive base package to the bottom surface of the acoustic stack and intersecting the second fin, thereby producing an ultrasound transducer having a flat front face comprising:
   a ground pad formed by the conductive base package;
   a signal pad formed by the matching layer; and
   a non-conductive groove separating the ground pad and the signal pad.

2. The method of claim 1, wherein the non-conductive groove is formed by the non-conductive glue.

3. The method of claim 1, wherein the comb structure is manufactured prior to laminating the comb structure and the conductive base package into the acoustic stack by dicing a layered stack with kerfs having depths equal to a height of the second fin.

4. The method of claim 1, wherein the comb structure and the conductive base package are interdigitated.

5. The method of claim 1, further comprising mounting the ultrasound transducer to a substrate by aligning the front face of the ultrasound transducer with a circuit printed on the substrate.

6. The method of claim 5, wherein the circuit includes a substrate ground pad, a substrate signal pad, and a separation line separating the substrate ground pad from the substrate signal pad, and wherein aligning the front face of the ultrasound transducer with the circuit includes aligning the non-conductive groove of the ultrasound transducer with the separation line.

7. The method of claim 1, wherein kerfs are diced into the conductive base package prior to laminating the comb structure and the conductive base package into the acoustic stack.

8. The method of claim 7, wherein the kerfs of the conductive base package have depths equal to a height of the first fin and widths greater than a width of the first fin.

9. The method of claim 1, wherein the ground pad is formed of one or more of graphite, porous graphite filled with resin, stainless steel, or aluminum.

10. The method of claim 1, wherein the ground pad is a surface of the conductive base package.

11. The method of claim 1, wherein the ground pad is electrically continuous with a bottom surface of the ultrasound transducer.

12. The method of claim 6, wherein aligning the front face of the ultrasound transducer with the circuit further includes aligning the substrate ground pad with the ground pad of the ultrasound transducer and the substrate signal pad with the signal pad of the ultrasound transducer.

13. The method of claim 6, wherein the circuit includes a copper layer configured as a mass of a spring-mass object and the matching layer is a spring of the spring-mass object, and wherein a resonant frequency of the spring-mass object falls within a range of a preferred bandwidth for a specific application of the ultrasound transducer.

* * * * *